(12) United States Patent
Secora

(10) Patent No.: US 7,819,802 B2
(45) Date of Patent: Oct. 26, 2010

(54) CATHETER TIP

(75) Inventor: Gary J. Secora, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 427 days.

(21) Appl. No.: 11/285,324

(22) Filed: Nov. 22, 2005

(65) Prior Publication Data

US 2007/0118035 A1     May 24, 2007

(51) Int. Cl.
| A61B 5/00 | (2006.01) |
| A61B 5/05 | (2006.01) |
| A61B 8/14 | (2006.01) |
| A61B 5/02 | (2006.01) |

(52) U.S. Cl. .................. 600/300; 600/407; 600/309; 600/466; 600/486

(58) Field of Classification Search .................. 600/300, 600/309, 407, 466, 486
See application file for complete search history.

(56) References Cited

U.S. PATENT DOCUMENTS

| 4,155,259 A | * | 5/1979 | Engeler ..................... 73/626 |
| 5,176,141 A | | 1/1993 | Bom et al. |
| 5,178,150 A | * | 1/1993 | Silverstein et al. .......... 600/463 |
| 5,240,003 A | * | 8/1993 | Lancee et al. ............... 600/467 |
| 5,325,860 A | | 7/1994 | Seward et al. |
| 5,345,940 A | | 9/1994 | Seward et al. |
| 5,375,602 A | | 12/1994 | Lancee et al. |
| 5,385,156 A | | 1/1995 | Oliva |
| 5,454,788 A | * | 10/1995 | Walker et al. ............ 604/99.04 |
| 5,505,088 A | * | 4/1996 | Chandraratna et al. ........ 73/623 |
| 5,699,805 A | | 12/1997 | Seward et al. |
| 5,704,361 A | | 1/1998 | Seward et al. |
| 5,713,363 A | | 2/1998 | Seward et al. |
| 5,788,636 A | | 8/1998 | Curley |
| 5,846,205 A | | 12/1998 | Curley et al. |
| 5,871,019 A | | 2/1999 | Belohlavek |
| 5,876,345 A | | 3/1999 | Eaton et al. |
| 5,938,616 A | | 8/1999 | Eaton et al. |
| 5,997,532 A | | 12/1999 | McLaughlin et al. |
| 6,039,693 A | | 3/2000 | Seward et al. |
| 6,099,475 A | | 8/2000 | Seward et al. |
| 6,129,672 A | | 10/2000 | Seward et al. |
| 6,149,599 A | | 11/2000 | Schlesinger et al. |
| 6,171,247 B1 | | 1/2001 | Seward et al. |
| 6,228,032 B1 | | 5/2001 | Eaton et al. |
| 6,248,072 B1 | | 6/2001 | Murkin |
| 6,306,096 B1 | | 10/2001 | Seward et al. |
| 6,415,046 B1 | | 7/2002 | Kerut, Sr. |
| 6,522,905 B2 | | 2/2003 | Desai |
| 6,611,699 B2 | | 8/2003 | Messing |
| 6,638,278 B2 | | 10/2003 | Falwell et al. |
| 6,645,147 B1 | | 11/2003 | Jackson et al. |

(Continued)

Primary Examiner—Patricia C Mallari

(57) ABSTRACT

A catheter tip of a catheter including at least a power conductor and a data conductor for obtaining data of a subject of interest. The catheter tip may comprise a support member defining an actuator sleeve, a sensor compartment, and a seal pocket. An actuator may be disposed in the actuator sleeve and coupled to the power conductor. A sensor may be disposed in the sensor compartment and coupled to the data conductor. A bearing/seal may be installed in the support member and coupled to the actuator and the sensor. A cover may be coupled to the support member and may define a transparent window exposing the sensor to the subject of interest, wherein the catheter tip may be coupled to the catheter in the seal pocket.

11 Claims, 4 Drawing Sheets

U.S. PATENT DOCUMENTS

| | | |
|---|---|---|
| 6,652,692 B2 | 11/2003 | Pedersen et al. |
| 6,663,625 B1 | 12/2003 | Ormsby et al. |
| 6,684,094 B1 | 1/2004 | Lehr et al. |
| 6,708,055 B2 | 3/2004 | Geiser et al. |
| 2005/0075554 A1 | 4/2005 | Bernhart et al. |
| 2005/0171591 A1 | 8/2005 | McHale et al. |

\* cited by examiner

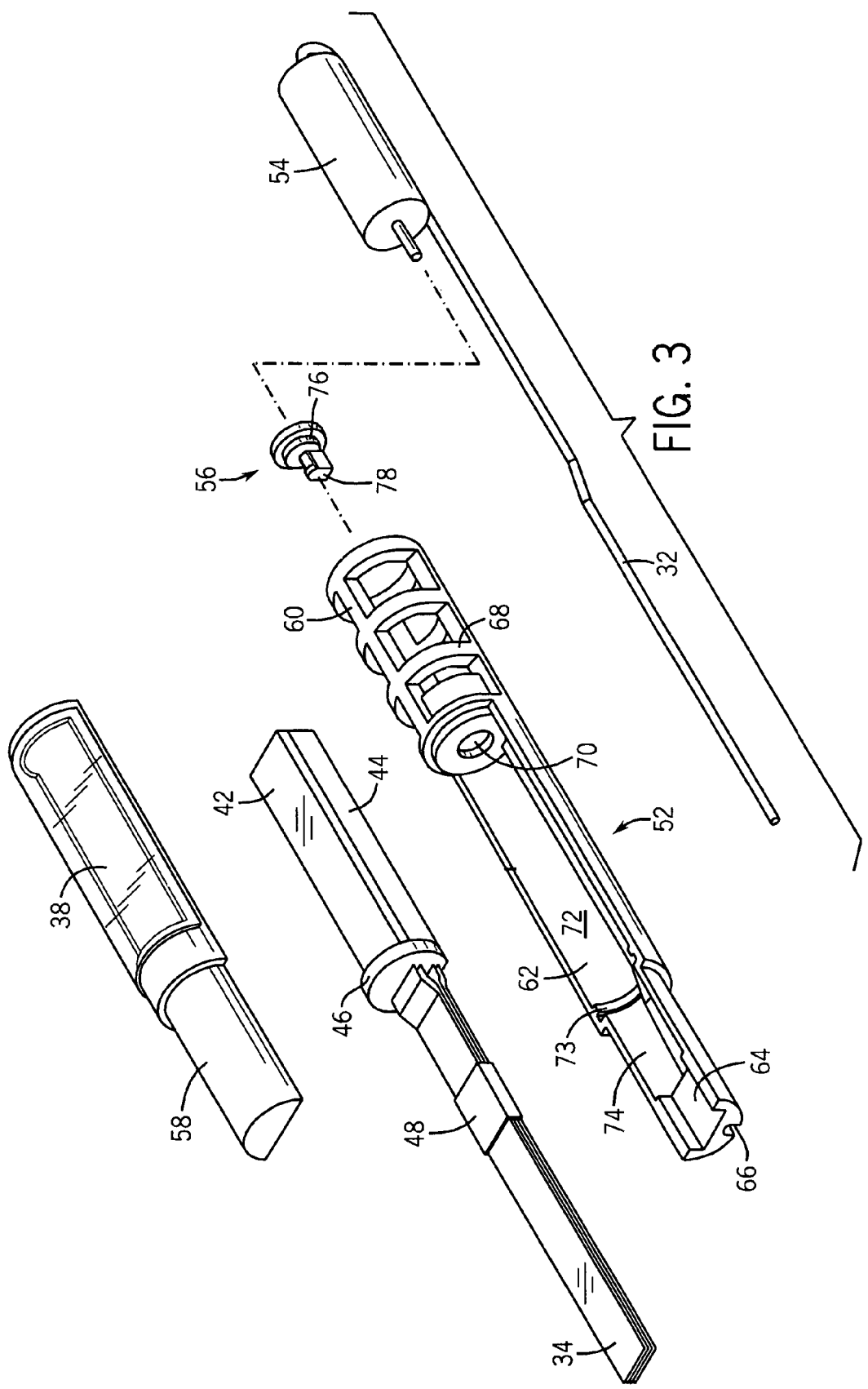

CATHETER TIP

BACKGROUND OF THE INVENTION

The present invention relates generally to the field of catheters and specifically to a catheter tip including a rotatable sensor.

Catheters are well known for use in guiding and diagnostic procedures, for example in medical procedures. Catheters can be used to transport various tools, such as stents, filters, other implantable medical devices. The catheter tip is the portion of the catheter that typically houses the operative device or devices that perform a procedure within the subject of interest, such as biological tissue, (e.g., a heart). In some circumstances, the catheter tip must be rotated in order to perform the desired function. Such rotation within the subject of interest can be hazardous to the catheter tip or to the subject of interest.

Thus there is a need for a catheter tip that transports a sensor capable of rotating within the catheter tip to transmit and receive data within the subject of interest. There is also a need for a catheter including a catheter tip that provides a rotating sensor for transmitting and receiving data within a subject of interest. There is also a need for a method of obtaining data from inside the subject of interest without requiring the rotation of the catheter or catheter tip itself.

SUMMARY OF THE INVENTION

One embodiment of the invention relates to a catheter tip configured to couple to a catheter including at least a power conductor and a data conductor for obtaining data of a subject of interest. The catheter tip comprises a support member defining an actuator sleeve, a sensor compartment, and a seal pocket. An actuator is disposed in the actuator sleeve and coupled to the power conductor. A sensor is disposed in the sensor compartment and coupled to the data conductor. A bearing/seal is installed in the support member and coupled to the actuator and the sensor. A cover is coupled to the support member and defines a transparent window exposing the sensor to the subject of interest, wherein the catheter tip is coupled to the catheter in the seal pocket.

Another embodiment of the invention relates to a catheter for insertion into a subject of interest. The catheter comprises an elongated body with a distal end and a proximal end, a handle coupled to the proximal end, a data conductor disposed in the elongated body and coupled to the handle, and a catheter tip disposed at the distal end of the elongated body. The catheter tip comprises a support member defining an actuator sleeve, a sensor compartment, and a seal pocket. An actuator is disposed in the actuator sleeve and coupled to the power conductor. A sensor is disposed in the sensor compartment and coupled to the data conductor. A bearing/seal is installed in the support member and coupled to the actuator and the sensor. A cover is coupled to the support member and defining a transparent window exposing the sensor to the subject of interest, wherein the catheter tip is coupled to the elongated body.

Another embodiment of the invention relates to a method of obtaining data from inside a subject of interest. The method comprises the steps of rotating a sensor of a catheter in at least one of a clockwise and counter-clockwise direction a predetermined number of degrees between zero and one hundred eighty degrees. The catheter includes a power conductor and a data conductor coupled to a catheter tip. The catheter tip includes the sensor coupled to an actuator and coupled to the data conductor and with the actuator coupled to the power conductor. Detecting data with the sensor at a target site inside the subject of interest. Transmitting the data over the data conductor for further processing.

BRIEF DESCRIPTION OF THE DRAWINGS

FIG. 3 is an exploded perspective view of a catheter tip according for use in the catheter of FIG. 1 according to one example embodiment.

DETAILED DESCRIPTION OF THE PREFERRED EMBODIMENTS

Figure 1:
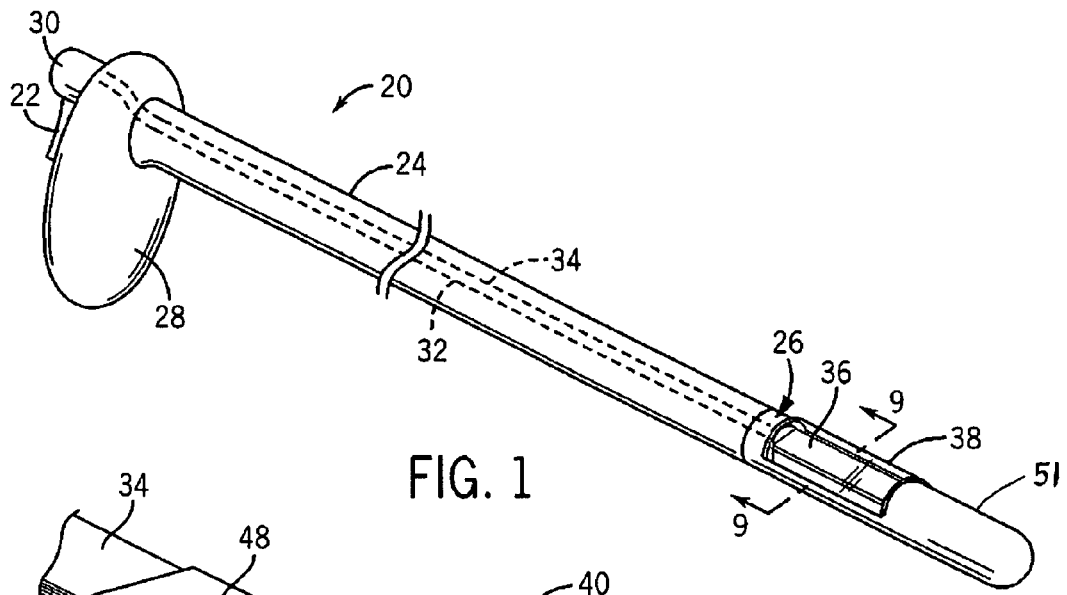
FIG. 1 is a side perspective view of a catheter according to one example embodiment.

FIG. 1 illustrates one example of a catheter 20 configured to obtain data from a subject of interest. In one example embodiment, the subject of interest may be a heart where catheter 20 is an intra-cardiac catheter used to retrieve data from inside the heart. Catheter 20 generally includes handle 22, shaft 24, and catheter tip 26. Handle 22 allows for gripping and controlling of catheter 20 by a user. Handle 22 includes a handle body 28 and control means 30. Handle body 28 is the actual portion of handle 22 that is grasped by a user. In one embodiment handle body 28 may be configured in an ergonomic fashion for comfort in the users hand. In other embodiments handle body 28 may be of any other form that facilitates gripping by a user such as a rectangular prism or ellipsoid shape.

Control means 30 is intended to serve as an interface for communication with catheter tip 26. A user may interact with control means 30 to determine what functions catheter tip 26 performs or to extend or retract catheter tip 26. In one example embodiment, control means 30 may be manipulated by a thumb of the user on the same hand that grips catheter 20. In other embodiments control means 30 may be manipulated by a free hand of the user. In other embodiments control means 30 may be manipulated robotically for a location remote from the control means 30.

Shaft 24 couples handle 22 to catheter tip 26 and is configured to enclose at least a power conductor 32 and a data conductor 34. Additional wires, for example a steering wire for guiding catheter tip 26, and a safety wire for retrieval of catheter tip 26, may also be enclosed in shaft 24 in some embodiments. Power conductor 32 is an electrical wire or bus that provides electrical power to catheter tip 26. Data conductor 34 is an electrical wire or bus that provides electric information signals to and receives electric information signals from catheter tip 26. In one example embodiment shaft 24 may enclose multiple power conductors and/or data conductors. In another example embodiment data conductor 34 may send and receive digital signal information. In still other embodiments data conductor 34 may send and receive analog signal information.

Catheter tip 26 is an overmolded portion of catheter 20 configured to perform the actual data retrieval from a subject of interest. Catheter tip 26 includes a sensor 36 and a window 38. Sensor 36 performs the data retrieval by sensing various conditions, factors, or attributes. Sensor 36 may be any type of sensor, including but not limited to a transducer or a probe, that is able to transmit and receive data. In one embodiment sensor 36 may be configured to emit and sense sound waves in a manner to facilitate ultrasonic imaging. In another embodiment, sensor 36 may detect infrared light waves to facilitate thermal imaging. In still other embodiments, sensor 36 may emit and sense radiation to facilitate X-ray imaging or may sense electric activity. While catheter tip 26 may be of any size, in one example embodiment, catheter tip 26 is approximately three millimeters in diameter.

Window 38 is a transparent portion of catheter tip 26 that allows light waves of one or more wavelengths—such as visible, infrared, and x-ray light waves, for example—and/or sound waves to pass through to and from exposed sensor 36. For purposes of this application transparent window means that window 38 is not opaque to the type of energy, e.g., sound, or light, being transmitted and received through window 38. Window 38 is configured to extend around a 180 degree portion of catheter tip 26. In some example embodiments, window 38 may extend around greater or less than a 180 degree portion of catheter tip 26.

Figure 2:
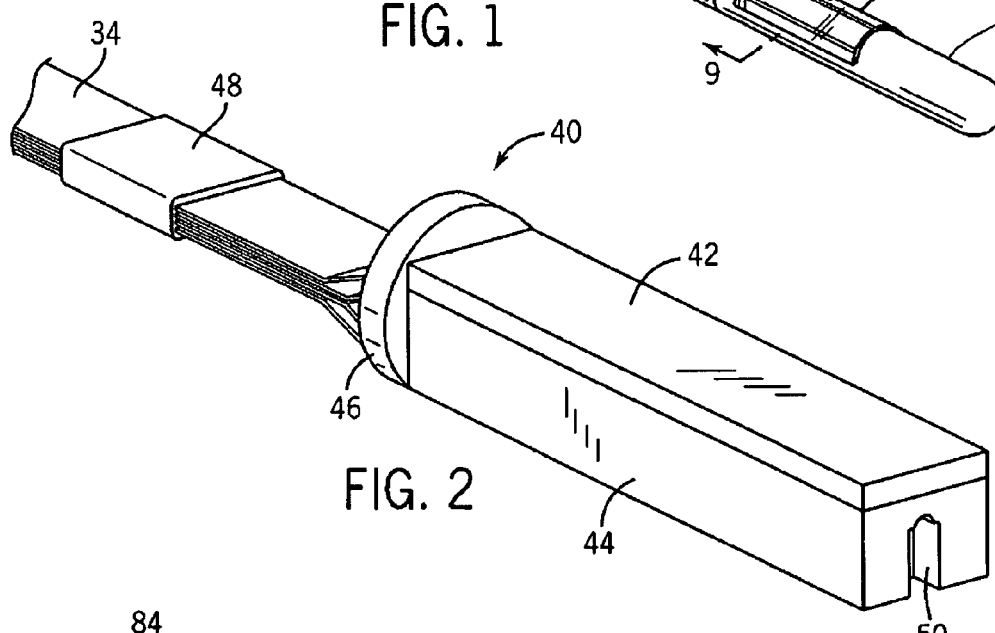
FIG. 2 is a perspective view of a sensor assembly used within the catheter of FIG. 1 according to one example embodiment.

FIG. 2 illustrates in detail an example embodiment of a sensor assembly 40. Sensor assembly 40 includes sensor array 42, sensor body 44, centering/mechanical support 46, and overmolded seal 48. Sensor array is the portion of sensor assembly made of exposed leads that retrieves the data from the subject of interest using one or more of any available data types (e.g. ultrasound), as given previously. The leads of sensor array 42 are coupled to and through sensor body 44 back to data conductors 34. Sensor body 44 serves as a mount for sensor array and defines notch 50. The sensor body 44 may be composed of one or more parts or portions coupled together. Notch 50 couples with an actuator, as will be described in greater detail below, so that sensor body, and thus sensor array, may be rotated for a wide range of data retrieval. This rotation is facilitated by centering/mechanical support, which is configured to maintain consistent centered rotation of sensor body 44 and sensor array 42. This consistent rotation will reduce the possibility that sensor body 44 and sensor array 42 will make contact with other portions of catheter tip 26 and thus prolong the life of sensor assembly 40. Overmolded seal 48 is a section of overmolding that serves to hold data conductors 34 together and to seal sensor assembly 40 within a support structure as given in detail below.

FIG. 3 illustrates an exploded view of catheter tip 26. Catheter tip 26 generally includes an overmold 51 (see FIG. 1) encasing the sensor assembly 40 (as described above), support member 52, an actuator 54, bearing/seal 56, and cover 58. Support member 52 functions to secure actuator 54 and sensor assembly 40 within catheter tip 26. Support member 52 defines an actuator sleeve 60, a sensor compartment 62, a seal pocket 64, and an actuator harness channel 66. In one example embodiment, support member 52 has a 2.8 millimeter outside diameter. In another embodiment, support member 52 may be made of a thermoplastic material. In other embodiments, support member 52 may be made of other materials such as metal, composite material, plastic, rubber, or a combination of such materials.

Actuator sleeve 60 encloses actuator 54 within support member 52. Actuator sleeve 60 may define one or more strengthening ribs 68, intended to promote a sturdy structure, and an opening 70, to allow for bearing/seal 56 to pass from actuator sleeve 60 to sensor compartment 62. While actuator sleeve 60 is shown have openings between strengthening ribs, in another embodiment, the actuator sleeve may be a continuous piece of material with strengthening ribs defined on the outer portion. In other embodiments, the actuator sleeve may secure the actuator without the use of strengthening ribs. While bearing/seal opening 70 is shown to be a round opening, in other embodiments, bearing/seal may be of any shape that allows bearing/seal 56 to pass from actuator sleeve 60 to sensor compartment 62 and still allow for rotation, centering of the sensor, and sealing of the compartment.

Sensor compartment 62 retains sensor assembly 40 in a secure and convenient manner. Sensor compartment 62 defines a section 72, a stop 73, and a section 74. According to an exemplary embodiments, section 72 may be wider than section 74. Section 72 is configured to hold sensor body 44, sensor array 42, and centering/mechanical support 46. Centering/mechanical support 46 is abutted to stop 73 and is intended to reduce the possibility of centering/mechanical support 46 sliding within section 72. Section 74 serves as reduced diameter area that allows for steering of data conductors 34 in a safe manner and to maintain consistent wall thickness of the catheter tip 26. Because the diameter of section 74 is reduced, data conductors 34 are retained in a secure fashion so that possibility of contact with other portions of catheter tip 26 is reduced. The reduced diameter of section 74 also provides in one embodiment an area for attachment of a steering and safety wires for the catheter 20. In other example embodiments, the width of section 74 may be substantially the same as section 72.

Seal pocket 64 seals sensor assembly 40 within catheter tip 26. Seal pocket 64 receives overmolded seal 48 of sensor assembly 40 and when cover 58 is placed over support member 52 sensor assembly 40 is substantially sealed within catheter tip 26. Overmolded seal 48 is made of an elastomeric material such as rubber and thus a seal is defined due to the snug fit of overmolded seal 48 within seal pocket 64 and to cover 58. In another example embodiments, seal pocket 64 may instead be a portion of cover 58.

Actuator harness channel 66, also sometimes referred to as a motor wire harness raceway or conduit, serves as a guide for power conductor 32, which connects to actuator 54. By placing actuator harness channel 66 on the under side of support member 52, power conductor 32 can to be safely run from actuator 54 to handle 22 with a reduced risk of a short that may occur if power conductor 32 would come into contact with sensor 36 or data conductor 34. In other example embodiments, actuator harness channel may be a sealed cavity through a substantially same portion of catheter tip 26 as sensor assembly 40.

Bearing/seal 56 is configured to couple actuator 54 with sensor assembly 40. The bearing/seal 56 rotates in discrete movements between zero and one hundred eighty degrees. Bearing/seal 56 includes a seal 76 and a drive pin 78. Seal 76 functions to separate actuator sleeve 60 from sensor compartment 62 so that the possibility of a short between actuator 54 and sensor assembly 40 is reduced and to prevent loss of coupling medium. Drive pin 78 couples actuator 54 to notch 50 of sensor assembly 40. Drive pin 78 is intended to be substantially secure within notch 50 so that when drive pin 78 rotates, sensor body 44 also rotates.

Actuator 54 is configured to rotate sensor body 44 and sensor array 42 in order to facilitate a wide area of data retrieval. Actuator 54 is powered by power conductor 32, which extends to handle 22 via actuator harness channel 66 as described above. Actuator may be of any configuration that facilitates rotation of drive pin 78. In one example embodiment, actuator 54 may be an electric stepper motor that functions to rotate a fixed amount upon receiving a power signal. The electric motor typically includes a motor wire harness that couples to the power conductor 32. In other embodiments, actuator 54 may be a solid state device that rotates drive pin based on the output of the digital logic therein. In still other example embodiments, actuator 54 may include a hydraulic or pneumatic motor.

Figure 4:
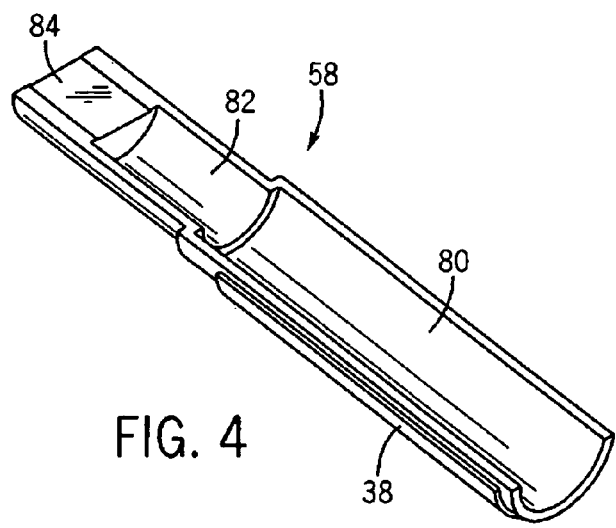
FIG. 4 is a perspective view of the under-side of the cover of FIG. 3 according to one example embodiment.

With reference to FIGS. 3 and 4, cover 58 is shown to fit over the top of sensor assembly 40 to enclose and seal sensor assembly 40 within support member 52. Cover 58 includes window 38, inner surface 80, section 82, and seal pocket 84. Window 38 is a transparent portion of cover 58 that allows light waves of one or more wavelengths—such as visible, infrared, and x-ray light waves, for example—to pass through to exposed sensor 36. Window 38 may also be permeable to sound waves. Window 38 is configured to extend around a 180 degree portion of catheter tip 26. In some example embodiments, window 38 may extend around greater or less than a 180 degree portion of catheter tip 26. In other example embodiments, cover 58 is 0.2 millimeters thick. Inner surface 80 is the counterpart to section 72 of support member 52 and encloses sensor assembly 40. Section 82 is the counterpart to section 74 of support member 52 and encloses and steers data conductors 34 in a safe manner. Seal pocket 84 is the counterpart to seal pocket 64 of support member 52 and aids in defining the seal around overmolded seal 48.

Figure 5:
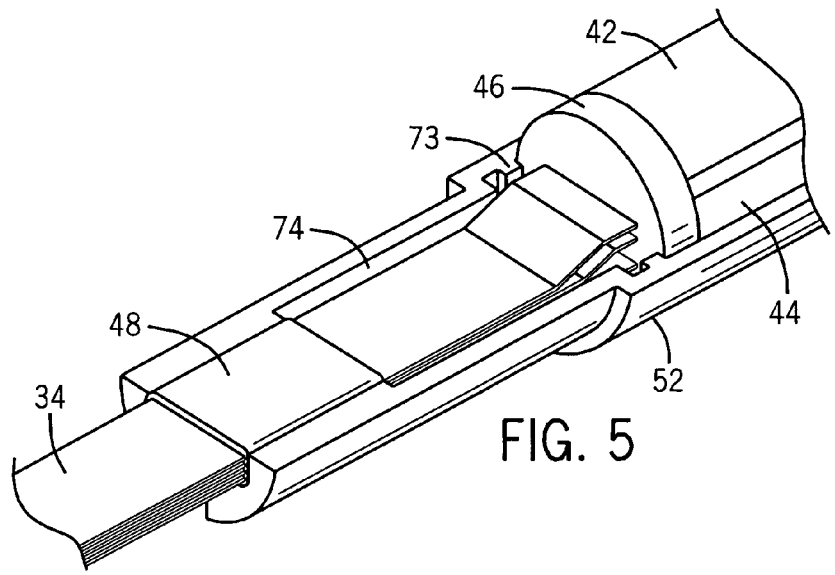
FIG. 5 is a perspective view of the support member of FIG. 3 with the sensor assembly of FIG. 2 inserted according to one example embodiment.

FIG. 5 illustrates in detail how sensor assembly 40 rests within support member 52. Sensor array 42, sensor body 44, and centering/mechanical support 46 rest within section 72. Data conductors 34 are steered within section 74 providing for safe connection to sensor array 42. Overmolded seal 48 rests in seal pocket 64 so that a substantially snug seal may be defined. Forming such a seal reduces the possibility that the outside environment becomes a factor and thus accurate data can be retrieved from sensor 36.

Figure 6:
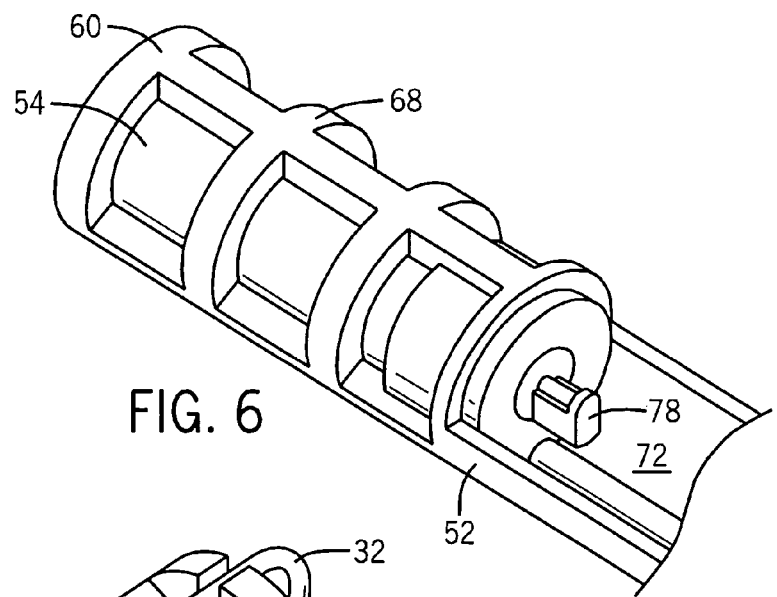
FIG. 6 is a top perspective view of an actuator inserted into the support member of FIG. 3 according to one example embodiment.
Figure 7:
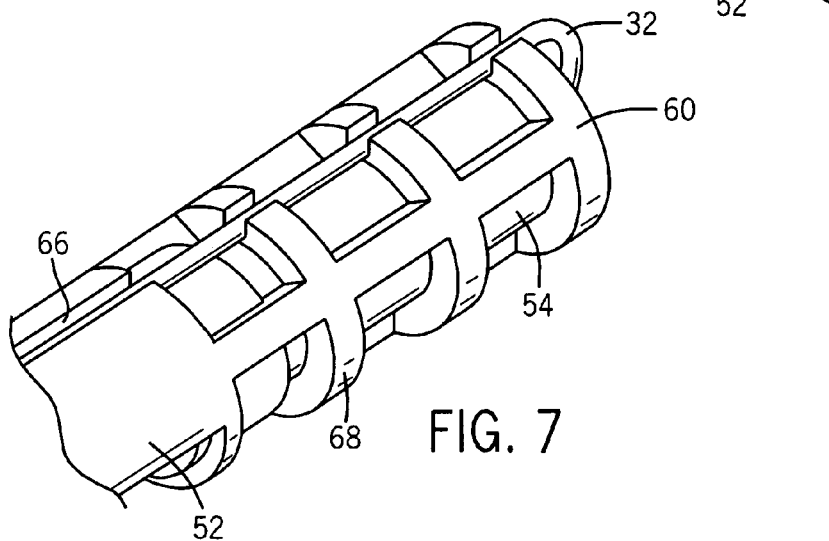
FIG. 7 is a bottom perspective view of an actuator inserted into the support member of FIG. 3 according to one example embodiment.
Figure 8:
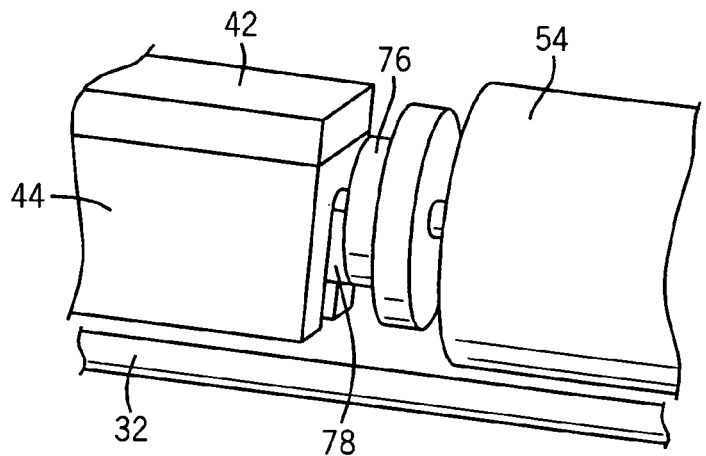
FIG. 8 is a side perspective view of the actuator of FIG. 3 coupling to the sensor assembly of FIG. 2 according to one example embodiment.

FIGS. 6-8 illustrate how actuator 54 and bearing/seal 56 interact within support member 52. Referring to FIG. 6, actuator 54 is secured within actuator support sleeve and pushes seal 76 against support member 52 so that actuator does not have contact with sensor assembly 40, reducing the possibility of a short or of noise from actuator 54 affecting the date retrieved by sensor array 42 and to seal in the coupling medium. By pushing seal 76 against support member 52, drive pin 78 is inserted through opening 70 so that sensor body 44 may be secured to actuator 54. Referring to FIG. 7, actuator harness channel 66 guides power conductor 32 along support member 52 to handle 22 away from other components of catheter tip 26 so that the possibilities of a short are reduced and so that noise from power conductor 32 does not affect data retrieval. Referring to FIG. 8, the coupling of bearing/seal 56 to actuator 54 is shown. Sensor body 44 is coupled to actuator 54 via drive pin 78, which is secured into notch 50, so that sensor body 44 and sensor array 42 may be rotated for a wide range of data retrieval.

Figure 9:
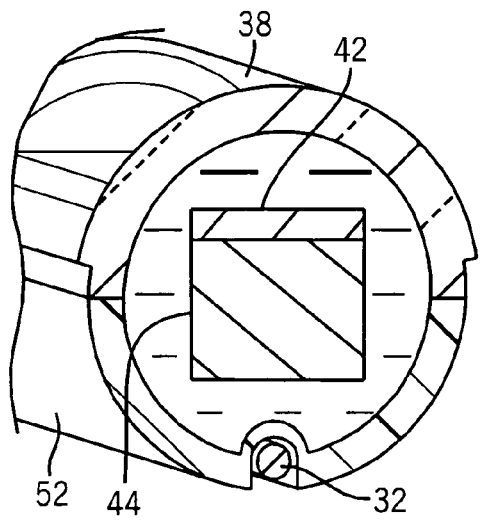
FIG. 9 is a perspective cross sectional view of the catheter tip of FIG. 1 according to one example embodiment.
Figure 10:
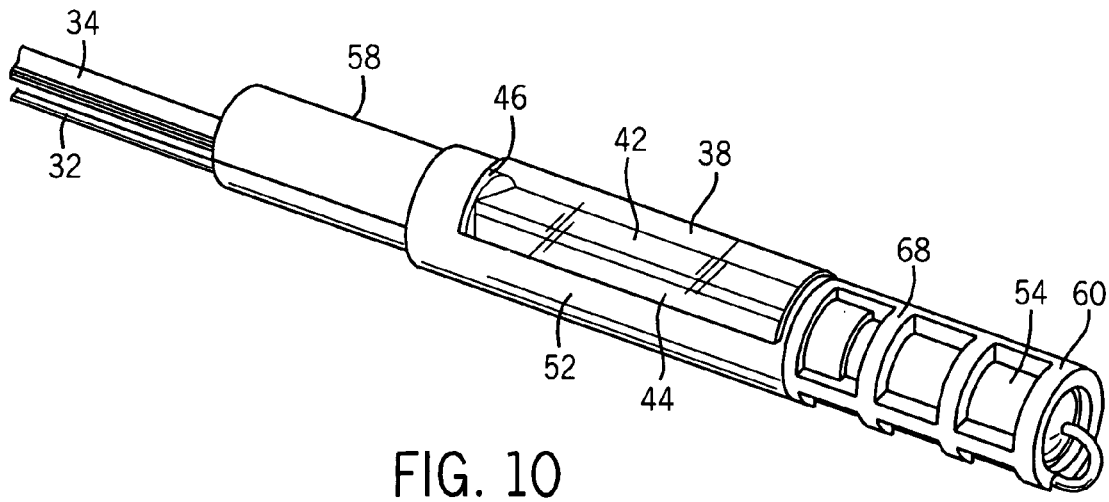
FIG. 10 is a transparent perspective view of the catheter tip of FIG. 1 according to one example embodiment.

FIGS. 9 and 10 illustrate an example embodiment of an assembled catheter tip 26 and the interaction of the individual elements therein. Referring to FIG. 9 sensor array 42 sensor body 44 fit within the cavity created by section 72 and inner surface 80 and how sensor array may be rotated within catheter tip 26. Actuator harness channel 66 retains power conductor 32 in such a manner that the general cylindrical shape of catheter tip 26 is not compromised. Actuator harness raceway is defined by an intrusion into catheter tip 26 rather than a protrusion from it in order to simplify the overmolding process of catheter tip 26 and save on overmolding material. Window 38 defines a portion of cover 58 that protrudes from cover for ease of manufacture. In other example embodiments, actuator harness raceway may be a protrusion from catheter tip 26. In another embodiment, window 38 may be integrally inlayed within the confines of the thickness of cover 58.

Referring to FIG. 10, the overmolded seal 48 is compressed by cover 58 onto seal pocket 64 creating a seal between the inside and outside of catheter tip 26 so that the outside environment's affect on any sensor readings is reduced. The cavity which holds sensor assembly 40 may be filled with a coupling medium. The coupling medium is intended to mechanically stabilize sensor 36 inside of catheter tip 26 and promote efficient sound and/or light wave propagation depending on the technology in use. In one example embodiment where sound waves are transmitted and received by sensor 36, the coupling medium may be any medium that has an acoustic impedance and carries the speed of sound similar to that of the human body, such as saline, water, oil, perfluorocarbon, or the like, for example. In another example where optical waves are transmitted and received by sensor 36, the coupling medium may be any medium that has an optical impedance and carries the speed of light similar to that of the human body. Window 38 exposes sensor array 42 to the subject of interest so that data may be retrieved throughout a 180 degree portion. This wide viewing angle may be used to facilitate a three dimensional volume of data. Data conductors 34 and power conductors 32 run from catheter tip 26 to handle as shown in FIG. 1 via sensor compartment and actuator harness raceway, respectively. When data is received from catheter tip 26, it may be further processed by a computer processing means including a visual display.

Although catheter 20 is illustrated as including multiple features utilized in conjunction with one another, catheter 20 may alternatively utilize less than all of the noted mechanisms or features. For example, in other embodiments, bearing/seal 56 may be a permanent attachment to actuator 54. In still other embodiments, centering/mechanical support 46 may be replaced by a centering/support feature integrated into support member 52 or omitted completely.

Although specific shapes of each element have been set forth in the drawings, each element may be of any other shape that facilitates the function to be performed by that element. For example, sensor body 44 and sensor array 42 are shown to define a rectangular prism, however, in other embodiments the structure may define that of a relatively cylindrical form.

For purposes of this disclosure, the term "coupled" means the joining of two components (electrical or mechanical) directly or indirectly to one another. Such joining may be stationary in nature or movable in nature. Such joining may be achieved with the two components (electrical or mechanical) and any additional intermediate members being integrally defined as a single unitary body with one another or with the two components or the two components and any additional member being attached to one another. Such joining may be permanent in nature or alternatively may be removable or releasable in nature The present disclosure has been described with reference to example embodiments, however workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

It is also important to note that the construction and arrangement of the elements of the system as shown in the preferred and other exemplary embodiments is illustrative only. Although only a certain number of embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the assemblies may be reversed or otherwise varied, the length or width of the structures and/or members or connectors or other elements of the system may be varied, the nature or number of adjustment or attachment positions provided between the elements may be varied. It should be noted that the elements and/or assemblies of the system may be constructed from any of a wide variety of materials that provide sufficient strength or durability. Accordingly, all such modifications are intended to be included within the scope of the present disclosure. Other substitutions, modifications, changes and omissions may be made in the design, operating conditions and arrangement of the preferred and other exemplary embodiments without departing from the spirit of the present subject matter.

What is claimed is:

1. A catheter for insertion into a subject of interest, the catheter comprising:
   an elongated body with a distal end and a proximal end;
   a handle coupled to the proximal end;
   a data conductor disposed in the elongated body and coupled to the handle;
   a power conductor disposed in the elongated body and coupled to the handle;
   a catheter tip disposed at the distal end of the elongated body, the catheter tip comprising:
      a support member defining an actuator sleeve, a sensor compartment and a seal pocket;
      an actuator disposed in the actuator sleeve and coupled to the power conductor;
      a sensor disposed in the sensor compartment and coupled to the data conductor;
      a bearing/seal installed in the support member and coupled to the actuator and the sensor; and
      a cover coupled to the support member and defining a transparent window exposing the sensor to the subject of interest wherein the catheter tip is coupled to the elongated body, wherein the elongated body includes a centering/mechanical support member configured to generally maintain centered rotation of the sensor within the support member.

2. The catheter of claim 1, wherein the bearing/seal is configured for rotational motion.

3. The catheter of claim 2, wherein the bearing/seal rotates in discrete movements between zero and one hundred eighty degrees.

4. The catheter of claim 1, including ribs on the actuator sleeve to protect the actuator.

5. The catheter of claim 1 including an overmold encasing the support member, cover, actuator, and sensor to a predetermined diameter, leaving the transparent window exposed.

6. The catheter of claim 1, wherein the actuator includes an electric motor and a motor wire harness, and wherein the electric motor is disposed at a distal end of the catheter tip.

7. The catheter of claim 6, wherein the support member includes a channel configured to receive the motor wire harness and guide the motor wire harness to the power conductor.

8. The catheter of claim 1, wherein the sensor is a transducer including a body and transducer array.

9. The catheter of claim 8, wherein the body defines a feature configured to couple with a drive pin of the bearing/seal to transmit a rotational force to the sensor.

10. A catheter of claim 1, wherein the catheter tip is coupled to the distal end of the elongated body.

11. A catheter for insertion into a subject of interest, the catheter comprising:
   an elongated body with a distal end and a proximal end;
   a handle coupled to the proximal end;
   a data conductor disposed in the elongated body and coupled to the handle;
   a power conductor disposed in the elongated body and coupled to the handle;
   a catheter tip disposed at the distal end of the elongated body, the catheter tip comprising:
      a support member defining an actuator sleeve, a sensor compartment and a seal pocket;
      an actuator disposed in the actuator sleeve and coupled to the power conductor;
      a sensor disposed in the sensor compartment and coupled to the data conductor;
      a bearing/seal installed in the support member and coupled to the actuator and the sensor, the bearing/seal including a drive pin; and
      a cover coupled to the support member and defining a transparent window exposing the sensor to the subject of interest wherein the catheter tip is coupled to the elongated body, wherein the elongated body defines a feature configured to couple with the drive pin of the bearing/seal to transmit a rotational force to the sensor.

* * * * *